United States Patent [19]
Suzuki et al.

[11] Patent Number: 5,342,843
[45] Date of Patent: Aug. 30, 1994

[54] THIENOIMIDAZOPPYRIDONE DERIVATIVES

[75] Inventors: Fumio Suzuki, Mishima; Yoshikazu Miwa, Sunto; Takeshi Kuroda, Itano; Shigeto Kitamura, Machida; Haruhiko Manabe, Sunto, all of Japan

[73] Assignee: Kyowa Hakko Kogyo Co., Ltd., Tokyo, Japan

[21] Appl. No.: 98,329

[22] PCT Filed: Dec. 8, 1992

[86] PCT No.: PCT/JP92/01602

§ 371 Date: Aug. 6, 1993

§ 102(e) Date: Aug. 6, 1993

[87] PCT Pub. No.: WO93/12116

PCT Pub. Date: Jun. 24, 1993

[30] Foreign Application Priority Data

Dec. 12, 1991 [JP] Japan ............... 3-329154

[51] Int. Cl.$^5$ .................. C07D 491/12; A61K 31/44
[52] U.S. Cl. ............................ 514/293; 546/83
[58] Field of Search ............... 546/83; 514/293

[56] References Cited
FOREIGN PATENT DOCUMENTS 0223420  5/1987  European Pat. Off. ............ 546/83

*Primary Examiner*—Alan L. Rotman
*Attorney, Agent, or Firm*—Fitzpatrick, Cella, Harper & Scinto

[57] ABSTRACT

The present invention relates to a thienoimidazopyridone derivative represented by Formula (I):

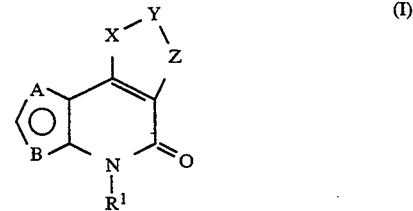

wherein A and B independently represent —S— or —CH=, X-Y-Z represents —N($R^2$)—CH=N— or —N=CH—N ($R^2$)— wherein $R^2$ is hydrogen, lower alkyl or —CH($R^3$)—(CH$_2$)$_n$—$R^4$ wherein $R^4$ is phenyl, n is 0 or 1, and $R^3$ is hydrogen or lower alkyl, and $R^1$ represents lower alkyl, or a pharmaceutically acceptable salt thereof.

4 Claims, No Drawings

THIENOIMIDAZOPPYRIDONE DERIVATIVES

TECHNICAL FIELD

The present invention relates to novel thienoimidazopyridone derivatives which possess excellent antiathsmatic (bronchodilator) activity and immunoregulatory activity and have a 1H, 5H- or 3H,5H-thieno[2,3-b]or [3,2-b]imidazo[4,5-d]pyridine-4-one skeleton.

PRIOR ART

A thienoimidazopyridine derivative represented by the formula:

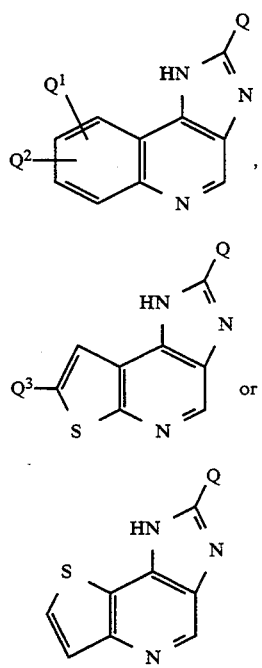

wherein Q is phenyl or a 5- or 6-membered heterocyclic group and $Q^1$, $Q^2$ and $Q^3$ are each independently hydrogen, halogen, alkyl or haloalkyl,
has been reported to possess psychotropic activity [Japanese Published Unexamined Patent Application No. 99069/1988 (EP-A-223420)].

DISCLOSURE OF THE INVENTION

The present invention relates to a thienoimidazopyridone derivative represented by the Formula (I):

(I)

wherein A and B independently represent —S— or —CH═, X-Y-Z represents —N($R^2$)—CH═N— or —N═CH—N($R^2$)— wherein $R^2$ is hydrogen, lower alkyl or —CH($R^3$)—(CH$_2$)$_n$—$R^4$ wherein $R^4$ is phenyl, n is 0 or 1, and $R^3$ is hydrogen or lower alkyl, and $R^1$ represents lower alkyl, or a pharmaceutically acceptable salt thereof.

In the definition of each group in Formula (I), the lower alkyl means a straight-chain or branched alkyl group having 1 to 6 carbon atoms, for example, methyl, ethyl, propyl, isopropyl, butyl, isobutyl, sec-butyl, tert-butyl, pentyl, neopentyl, and hexyl.

The pharmaceutically acceptable salt of Compound (I) may be any pharmaceutically acceptable acid addition salt, for example, an inorganic acid salt such as hydrochloride, sulfate, and phosphate, or an organic acid salt such as acetate, maleate, fumarate, tartrate, and citrate.

Hereinafter, a compound represented by the Formula (I) is referred to as Compound (I), and the same shall apply to the compounds represented by other formulas.

The process for preparing Compound (I) is shown below.

Compound (I) wherein $R^2$ is hydrogen may exist as either tautomer Compound (I-1) or Compound (I-2), and hereafter, each of Compound (I-1) and Compound (I-2) is referred to as Compound (I-1).

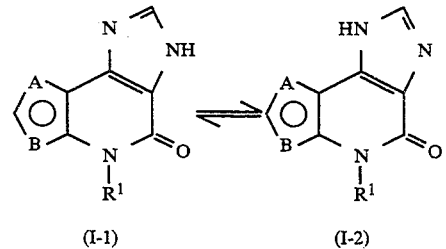

(I-1)      (I-2)

Method 1

Compound (IA), Compound (I) wherein X-Y-Z is —N($R^2$)—CH═N—, may be obtained by the following reaction steps.

The starting Compound (II) may be synthesized by the method described in References 1-1) to 1-4).

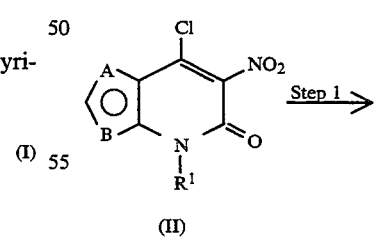

(II)

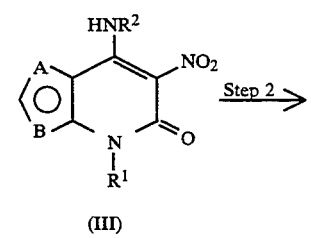

(III)

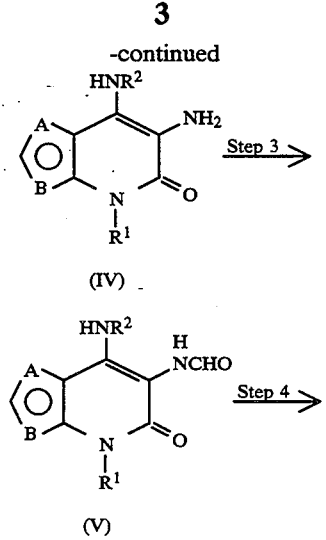

(IV)

(V)

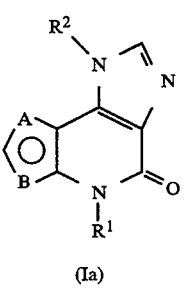

(Ia)

wherein A, B, $R^1$ and $R^2$ have the same meanings as defined above.

Step 1

Compound (III) may be obtained by reacting Compound (II) with amine (VI) represented by the formula $$R^2NH_2 \qquad \qquad (VI)$$

wherein $R^2$ has the same meaning as defined above, in the presence or in the absence of a solvent and, if necessary, in the presence of a base.

The bases used in the reaction include alkali metal carbonates such as potassium carbonate, and sodium carbonate; alkali metal hydrides such as sodium hydride; alkyl metal alkoxides such as sodium methoxide, sodium ethoxide; and alkylamines such as triethylamine.

As the solvent, any solvent may be used, as long as it is inert to the reaction. For example, an ether such as tetrahydrofuran, and dioxane, an amide such as dimethylformamide, an alcohol such as methanol, and ethanol, a hydrocarbon such as xylene, toluene, n-hexane, and cyclohexane, a haloalkane such as chloroform, and carbontetrachloride, or dimethylsulfoxide may be used singly or in combination. The reaction is carried out at 0°–100° C., and is completed in 5 minutes to 24 hours.

Step 2

Compound (IV) may be obtained by reducing Compound (III) in a solvent. As the reduction method, catalytic reduction using palladium/carbon and platinum oxide, or reduction using a metal sulfur derivative such as sodium hydrosulfite, may be employed.

As the solvent, any solvent may be used, as long as it is inert to the reaction. For example, an ether such as tetrahydrofuran, and dioxane, an amide such as dimethylformamide, an alcohol such as methanol, and ethanol, an acid such as hydrochloric acid, acetic acid, and sulfuric acid, or water may be used singly or in combination. The reaction is carried out at 0°–100° C., and is completed in 5 minutes to 24 hours.

Step 3

Compound (V) may be obtained by reacting Compound (IV) with formic acid or a reactive derivative thereof.

When formic acid is used, the reaction is preferably carried out in the presence of a condenser, and as the condenser, there may be used thionil chloride, N,N'-dicyclohexylcarbodiimide (DCC), polyphosphoric acid, etc. The reactive derivative used may be a mixed acid anhydrate produced by reacting formic acid with an acid halide such as an acid chloride or acid bromide, an acid anhydrate or an ethyl chlorocarbonate and isobutyl chlorocarbonate, or active esters of formic acid, such as p-nitrophenyl ester, imido N-oxysuccinimido ester, etc., and orthoesters, etc. The reaction is carried out at −10° to 50° C. and is completed in 5 minutes to 24 hours.

Step 4

Compound (Ia) may be obtained by treating Compound (V) in the presence or in the absence of a solvent, and if necessary, in the presence of a cyclizing agent.

Examples of the reaction solvent include hexamethylphosphoramide, diphenyl ether, glycerine triethyl ether, butyl ether, isoamyl ether, diethylene glycol, triethylene glycol, Dowtherm A (manufactured by Dow Chemical Co.). The cyclizing agent may be polyphosphoric acid, polyphosphoric acid ester, sulfuric acid, acetic acid, phosphorus pentachloride, phosphorus oxychloride, phosphorus trichloride, phosphorus tribromide, thionyl chloride, etc. The reaction is carried out at 50°–250° C., preferably at 100°–250° C., and is completed in 5 minutes to 24 hours.

Method 2

Compound (Ib) [Compound (I) wherein X-Y-Z is —N═CH—N($R^{2a}$)] may be obtained by reacting Compound (I-1) represented by the formula given below with Compound (VII) represented by the formula given below in the presence of a solvent, and preferably in the presence of a base, according to the following reaction step.

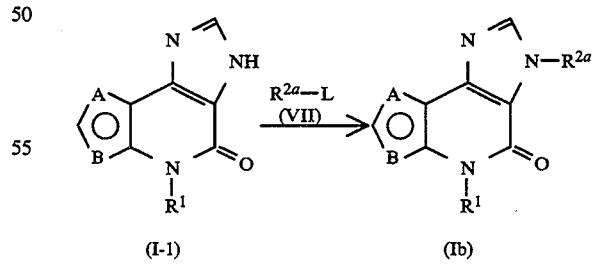

(I-1)      (Ib)

wherein L is a leaving group, $R^{2a}$ is any group according to the definition of $R^2$ except hydrogen, and A, B and $R^1$ have the same meaning as defined above.

Examples of the leaving group represented by L include a halogen atom such as chlorine, bromine, and iodine, an alkylsulfonyloxy group such as methanesulfonyloxy, and arylsulfonyloxy group such as phenylsulfonyloxy and p-toluenesulfonyloxy.

Examples of the base include alkali metal carbonates such as potassium carbonate and sodium carbonate, alkali metal hydrides such as sodium hydride, alkyl metal alkoxides such as sodium methoxide and sodium ethoxide, and alkylamines such as triethylamine.

As the solvent, those which are inert to the reaction, for example, ethers such as tetrahydrofuran and dioxane, amides such as dimethylformamide, alcohols such as methanol and ethanol, hydrocarbons such as xylene, toluene, n-hexane and cyclohexane, a haloalkanes such as chloroform and carbontetrachloride, and dimethylsulfoxide, may be used singly or in combination. The reaction is carried out at 0°–200° C., and is completed in 5 minutes to 24 hours.

The intermediates or desired compounds in the processes described above may be isolated and purified by purification means such as filtering, extraction, washing, drying, concentration, recrystallization, and various kinds of chromatography. The obtained intermediates may also be subjected to the subsequent reactions without purification.

In the case where a salt of Compound (I) is desired and it is produced in the form of the desired salt, it may be subjected to purification as such. In the case where Compound (I) is produced in the free form and its salt is desired, it may be dissolved or suspended in an appropriate solvent, and then an acid may be added thereto.

Compound (I) and pharmaceutically acceptable salts thereof may exist in the form of an addition product with water or with a solvent. Such addition products are also included in the scope of the present invention.

Specific examples of Compound (I) obtained in the respective processes are listed in Tables 1 and 2.

The compound numbers 1, 2, 3 ... in the tables correspond to the compounds obtained in Examples 1, 2, 3 ... described hereafter, and this applies to all subsequent tables.

TABLE 1

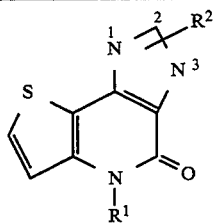

| Compound No. | $R^1$ | $R^2$ |
|---|---|---|
| 1 | $(CH_2)_3CH_3$ | 3-H |
| 2 | $(CH_2)_3CH_3$ | 3-$CH_3$ |
| 3 | $(CH_2)_3CH_3$ | 3-$CH_2Ph$ |
| 4 | $(CH_2)_3CH_3$ | 1-$CH_3$ |
| 5 | $(CH_2)_3CH_3$ | 1-$CH_2Ph$ |
| 6 | $CH(CH_3)_2$ | 3-H |
| 7 | $CH(CH_3)_2$ | 3-$CH_3$ |
| 8 | $CH(CH_3)_2$ | 3-$CH_2Ph$ |
| 9 | $CH(CH_3)_2$ | 1-$CH_3$ |
| 10 | $CH(CH_3)_2$ | 1-$CH_2Ph$ |
| 11 | $(CH_2)_2CH_3$ | 3-H |
| 12 | $(CH_2)_2CH_3$ | 3-$CH_3$ |
| 13 | $(CH_2)_2CH_3$ | 3-$CH_2Ph$ |
| 14 | $(CH_2)_2CH_3$ | 1-$CH_3$ |
| 15 | $(CH_2)_2CH_3$ | 1-$CH_2Ph$ |
| 16 | $CH_2CH_3$ | 3-H |
| 17 | $CH_2CH_3$ | 3-$CH_3$ |
| 18 | $CH_2CH_3$ | 3-$CH_2Ph$ |
| 19 | $CH_2CH_3$ | 1-$CH_3$ |
| 20 | $CH_2CH_3$ | 1-$CH_2Ph$ |
| 21 | $CH_3$ | 3-H |
| 22 | $CH_3$ | 3-$CH_3$ |
| 23 | $CH_3$ | 3-$CH_2Ph$ |

TABLE 1-continued

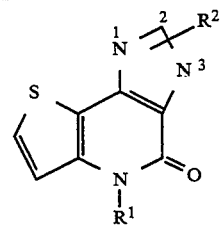

| Compound No. | $R^1$ | $R^2$ |
|---|---|---|
| 24 | $CH_3$ | 1-$CH_3$ |
| 25 | $CH_3$ | 1-$CH_2Ph$ |
| 26 | $CH_2CH(CH_3)_2$ | 3-H |
| 27 | $CH_2CH(CH_3)_2$ | 3-$CH_3$ |
| 28 | $CH_2CH(CH_3)_2$ | 3-$CH_2Ph$ |
| 29 | $CH_2CH(CH_3)_2$ | 1-$CH_3$ |
| 30 | $CH_2CH(CH_3)_2$ | 1-$CH_2Ph$ |

Ph represents a phenyl group.

TABLE 2

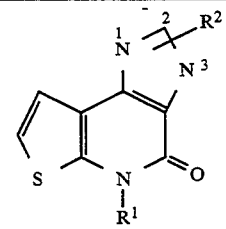

| Compound No. | $R^1$ | $R^2$ |
|---|---|---|
| 31 | $(CH_2)_3CH_3$ | 3-H |
| 32 | $(CH_2)_3CH_3$ | 3-$CH_3$ |
| 33 | $(CH_2)_3CH_3$ | 3-$CH_2Ph$ |
| 34 | $(CH_2)_3CH_3$ | 1-$CH_3$ |
| 35 | $(CH_2)_3CH_3$ | 1-$CH_2Ph$ |
| 36 | $(CH_2)_2CH_3$ | 3-H |
| 37 | $(CH_2)_2CH_3$ | 3-$CH_3$ |
| 38 | $(CH_2)_2CH_3$ | 3-$CH_2Ph$ |
| 39 | $(CH_2)_2CH_3$ | 1-$CH_2Ph$ |

Ph represents a phenyl group.

The pharmacological activities of Compounds (I) against passive Schulz-Dale reaction is shown in Experiment 1.

EXPERIMENT 1

Rabbit anti-OA serum prepared in advance by the method of Kohda, et al. [Folia Pharmacol. Japan, Vol. 66, p. 237 (1970)], was intraperitoneally administered to male Hartley guinea pigs weighing 350–500 g for passive sensitization, and 24 hours later tracheas of the animals were removed, and used for the following test. The tracheas were cut into zig-zag strips by the method of Emmerson and Mackay [J. Pharm. Pharmacol., Vol. 31, p.798 (1979)], were suspended in Krebs-Hensleit solution at 37° C. under aeration of a gas mixture of 95% oxygen and 5% carbon dioxide, and equilibrated for about 1 hour. The antigen, ovalbumin, was added to a bath (final concentration; 1 µg/ml). The contraction was recorded using an isotonic transducers (TD-112S; Nihon Koden Kogyo Co.) connected to a recorder (TYPE 3066; Yokogawa Hokushin Electric). Following the contraction curves reached a plateau, a test compound was cumulatively added in order to calculate the concentration causing 50% relaxation ($IC_{50}$) which was determined from least-squares regression analysis.

The results are shown in Table 3.

The inhibiting effect of Compound (I) on plaque-forming cells (PFC) is shown in Experiment 2.

Experiment 2

The method devised by Jerne, et al. [Science, Vol. 140, p.405 (1963)] was followed while referring to the method of Yamamoto, et al. [Drugs Exptl. Clin. Res., Vol. 8, p.5 (1982)]. That is, Balb/c strain male mice (7-week-old/SLC) were sensitized with $1 \times 10^8$ sheep erythrocytes (manufactured by Bio Test Research Institute), and the spleen was extirpated on the 6th or 7th day. The erythrocytes were removed using ACT solution [Tris (hydroxymethyl) aminomethane-$NH_4Cl$ solution] from the spleen cells, and were washed with RPMI-1640 medium (manufactured by Nissui Seiyaku Co.) three times. Suspensions of the obtained cells ($1 \times 10^7$) and the sheep erythrocytes ($5 \times 10^6$) were suspended with RPMI-1640 medium containing the test compound, 2-mercaptoethanol ($5 \times 10^{-5}$M), 10% bovine fetal serum (manufactured by Gibco Co.), streptomycin and penicillin. The obtained cell suspension was distributed into a 24-well microculture plate, and cultured in a carbon dioxide gas incubator at 37° C. for 5 days.

After the completion of culturing, the cells were transferred to a plastic test tube. They are centrifuged at 2000 rpm and the supernatant was removed. Then, the cells were further suspended in 1 ml of RPMI-1640. The cell suspension was charged, together with the sheep erythrocytes and the guinea pig complements, into a Cunningham chamber (manufactured by Takahashi Giken Co.), by the method of Cunningham, et al. [Immunology, Vol. 14, p.599 (1968)]. The cells were incubated at 37° C. for 1-2 hours, and then a direct PFC count was determined.

The results are shown in Table 3.

TABLE 3

| Compound No. | Passive Schultz-Dale reaction ($IC_{50}$, $\mu M$) | PFC inhibition rate (%) (concentration: $10^{-5}$ M) |
|---|---|---|
| 1 | 4.63 | 39.3 |
| 2 | 12.2 | 43.3 |
| 3 | — | 92.4 |
| 6 | 2.67 | 8.8 |
| 7 | 3.53 | 29.5 |
| 9 | 7.29 | 23.8 |
| 11 | 0.922 | — |
| 12 | 2.95 | 60.4 |
| 13 | — | 68.3 |
| 14 | 6.56 | — |
| 16 | 0.657 | 83.1 |
| 17 | 10.5 | 47.0 |
| 19 | 9.98 | — |
| 20 | 3.41 | — |
| 31 | 0.416 | −10.9 |
| 32 | 0.854 | 16.5 |
| 33 | 36.9 | 94.8 |
| 34 | 8.98 | −16.5 |
| 35 | 6.06 | −3.8 |
| 39 | 2.39 | — |

Note:
—: not measured

As shown in the experiment, Compound (I) exhibits a bronchodilatory effect and an immunoregulatory effect, and may therefore be expected to be useful as a treatment for bronchial diseases such as athsma.

Compound (I) and pharmaceutically acceptable salts thereof may be used as they are or in various preparation forms. The pharmaceutical composition of the present invention can be prepared by uniformly mixing Compound (I) or a pharmaceutically acceptable salt thereof as an active ingredient in an effective amount with pharmaceutically acceptable carriers. The pharmaceutical compositions are desirably in a single dose unit for oral or parenteral administration. Furthermore, Compound (I) may be administered by inhalation in the form of aerosol, finely pulverized powders or spraying solution.

In preparing the composition for oral administration, any pharmaceutically acceptable carriers which are useful may be used. For example, liquid preparations for oral administration such as a suspension and a syrup may be prepared using water; sugars such as, sucrose, sorbitol and fructose; glycols such as polyethylene glycol and propylene glycol; oils such as sesame oil, olive oil and soybean oil; preservatives such as p-hydroxybenzoate; or flavors such as strawberry flavor and peppermint flavor. Powders, pills, capsules and tablets may be prepared using excipient such as lactose, glucose, sucrose and mannitol; disintegrators such as starch and sodium alginate; lubricants such as magnesium stearate and talc; binders such as polyvinyl alcohol, hydroxypropyl cellulose and gelatin; surfactants such as fatty acid ester; or plasticizers such as glycerine. Tablets and capsules are the most useful single dose units for oral administration since their administration is easy. Solid pharmaceutical carriers are used in preparing tablets or capsules.

A solution for parenteral administration may be prepared using carriers such as distilled water, a saline solution, a glucose solution and a mixture of a saline solution and a glucose solution. In the case of aerosol administration, it is preferable to use a sprayer with a measuring bulb for release of a fixed effective dosage. This type of sprayer may be prepared by filling a container equipped with an aerosol bulb suitable for releasing the composition, with an aerosol composition obtained by dissolving the present compound in an appropriate pharmaceutically acceptable solvent, for example, ethyl alcohol, or a combination of miscible solvents, and mixing the solution with a pharmaceutically acceptable propellant.

The effective dose and the administration schedule of Compound (I) or pharmaceutically acceptable salts thereof vary depending on mode of administration, age, weight and conditions of a patient, etc., but it is generally preferred to administer the effective compound in a dose of 1-50 mg/kg per day in 1-3 parts.

BEST MODE FOR CARRYING OUT THE INVENTION

Examples and Reference Examples are shown below.

EXAMPLE 1

5-n-butylthieno[3,2-b]-3H-imidazo[4,5-d]pyridine-4(5H)-one (Compound 1)

To a methanol solution (75 ml) containing 2.05 g (7.63 mmol) of Compound (a) obtained in Reference Example 1 was added 400 mg of 10% palladium/carbon. The mixture was stirred under hydrogen atmosphere at 25° C. for 6 hours. The catalyst was removed by filtration using a filtering aid, and the filtrate was concentrated to obtain 6,7-diamino-4-n-butylthieno[3,2-b]pyridine-5(4H)-one. The obtained crude product was heated to reflux in 45 ml of ethyl orthoformate for 5 hours. After cooling, it was added to 1N aqueous hydrochloric acid, and washed with chloroform. The aqueous layer was made alkaline with 1N aqueous sodium hydroxide, and then extracted with chloroform. The organic layer was dried over anhydrous sodium sulfate, and then concentrated to dryness. The resulting residue was recrystallized from ethyl acetate to obtain 548 mg (30.9%) of Compound 1.

Melting point: 245.0°–246.0° C.
MS (EI) m/e: 247 (M+).
IR(KBr)cm$^{-1}$: 1645, 1459, 1436, 1380, 1266, 1228, 953.
NMR(DMSO-d$_6$)δ(ppm): 13.54 (1H, br), 8.20 (1H, s), 7.77 (1H, d, J=5.4 Hz), 4.41 (1H, d, J=5.4 Hz), 4.29 (2H, t, J=7.3 Hz), 1.65 (2H, m), 1.38 (2H, m), 0.93 (3H, t, J=7.3Hz).

EXAMPLE 2

5-n-butyl-3-methylthieno[3,2-b]-3H-imidazo[4,5-d]pyridine-4(5H)-one (Compound 2)

To N,N-dimethylformamide (DMF; 30 ml) solution containing 548 mg (2.22 mmol) of Compound 1 was added 60 mg (2.40 mmol) of sodium hydride. The mixture was stirred at 25° C. for 30 minutes. To the resulting solution was added 0.31 ml (5.00 mmol) of methyl iodide, and the mixture was further stirred at 25° C. for an hour. The reaction solution was concentrated and then added to water and extracted with chloroform. The organic layer was dried over anhydrous sodium sulfate, and concentrated to dryness. The resulting residue was purified by silica gel column chromatography to obtain 507 mg (87.5%) of Compound 2.

Melting point: 140.0°–144.5° C.
MS(EI)m/e: 261 (M+).
IR(KBr)cm$^1$: 1630, 1546, 1502, 1451, 1421, 1253, 1072, 780.
NMR(DMSO-d$_6$)δ(ppm): 8.03(1H, s), 7.90(1H, d, J=5.5Hz), 7.45(1H, d, J=5.5Hz), 4.26(2H, t, J=7.4 Hz), 4.23 (3H, s), 1.62 (2H, m), 1.36 (2H, m), 0.92 (3H, t, J=7.3Hz)

EXAMPLE 3

3-benzyl-5-n-butylthieno [3,2-b]-3H-imidazo [4,5-d]pyridine-4 (5H)-one (Compound 3)

To 100 ml of DMF solution containing 1.74 g (7.04 mmol) of Compound 1 was added 420 mg (10.5 mmol) of sodium hydride. The mixture was stirred at 25° C. for 30 minutes. To the resulting solution was added 1.70 ml (14.0 mmol) of benzyl bromide, and the mixture was further stirred at 25° C. for an hour. The resulting reaction solution was concentrated and then added to water and extracted with chloroform. The organic layer was dried over anhydrous sodium sulfate, and concentrated to dryness. The resulting residue was purified by silica gel column chromatography and treated with hydrochloric acid in ethyl acetate to obtain 1.24 g (47.1%) of hydrochloride of Compound 3.

Melting point: 219.0°–223.5° C.
MS(EI)m/e: 337 (M+).
IR(KBr)cm$^{-1}$: 1657, 1605, 1521, 769, 643.
NMR(DMSO-d$_6$)δ(ppm): 8.81(1H, s), 7.88(1H, d, J=5.4 Hz), 7.46(1H, d, J=5.4 Hz), 7.26–7.41(5H, m), 5.79 (2H, s), 4.27 (2H, t, J=7.5Hz), 1.57–1.68 (2H, m), 1.29–1.43 (2H, m), 0.91 (3H, t, J=7.4 Hz).

EXAMPLE 4

5-n-butyl-1-methylthieno[3,2-b]-1H-imidazo[4,5-d]pyridine-4(5H)-one (Compound 4)

To 40 ml of 1,2-dichloroethane solution containing 2.14 g (7.45 mmol) of Compound (a-4) obtained in the course of synthesis in Reference Example 1 were added 1.56 ml (11.2 mmol) of triethylamine and 503 mg (7.45 mmol) of methylamine monohydrochloride. The mixture was stirred at room temperature for 2 hours. The reaction mixture was then added to 1N aqueous sodium hydroxide and extracted with chloroform. The extract was dried over anhydrous sodium sulfate. The residue obtained by concentration was purified by silica gel column chromatography to obtain 2.10 g (100%) of a methylamino derivative of Compound (a).

In the same manner as in Example 1, a methylamino derivative of Compound (a) and formamide were used in place of Compound (a) and ethyl orthoformate to obtain 2.20 g (51.9%) of Compound 4.

Melting point: 150° 153° C.
MS(EI)m/e: 261 (M+).
IR(KBr)cm$^{-1}$: 1646, 1584, 1547, 1422, 1248, 1064, 720, 633.
NMR(DMSO-d$_6$)δ(ppm): 8.04 (1H, s), 7.92 (1H, d, J=5.4 Hz), 7.47 (1H, d, J=5.4 Hz), 4.26 (2H, t, J=7.4 Hz), 3.96 (3H, s), 1.55–1.66 (2H, m), 1.31–1.40 (2H, m), 0.91 (3H, t, J=7.3Hz)

EXAMPLE 5

1-benzyl-5-n-butylthieno [3,2-b]-1H-imidazo [4,5d]pyridine-4 (SH)-one (Compound 5)

In the same manner as in Example 4, benzylamine was used in place of methylamine monohydrochloric acid to obtain 2.43 g (91.5%) of a benzylamino derivative of Compound (a).

In the same manner as in Example 1, a benzylamino derivative of Compound (a) was used in place of Compound (a) to obtain 570 mg (24.8%) of Compound 5.

Melting point: 220°–225° C.
MS (EI) m/e: 337 (M+).
IR(KBr)cm$^{-1}$: 1642, 1579, 1547, 1497, 1451, 1426, 1372, 1248, 1103, 1067, 780, 724, 648.
NMR(DMSO-d$_6$)δ(ppm): 8.27 (1H, s), 7.81 (1H, d, J=5.4 Hz), 7.41 (1H, d, J=5.4 Hz), 7.20–7.39 (1H, m), 7.35 (2H, d, J=7.4 Hz), 7.18 (2H, d, J=7.4 Hz.), 5.61 (2H, s), 4.24 (2H, t, J=7.4 Hz), 1.56–1.65 (2H, m), 1.31–1.37 (2H, m), 0.90 (3H, t, J=7.4 Hz).

EXAMPLE 6

5-isopropylthieno [3,2-b]-3H-imidazo [4,5-d]pyridine-4 (5H)-one (Compound 6)

In the same manner as in Example 1, 0.68 g (2.68 mmol) of Compound (b) obtained in Reference Example 2 was used in place of Compound (a) to obtain 0.53 g (84.6%) of Compound 6.

Melting point: >300° C.
MS (EI) m/e: 233 (M+).
IR(KBr)cm$^{-1}$: 1646, 1572, 1444, 1230, 1159, 955, 853, 777, 626.
NMR(DMSO-d$_6$)δ(ppm): 13.49 (1H, br), 8.19 (1H, s), 7.76 (1H, d, J=5.4 Hz), 7.61 (1H, d, J=5.4 Hz), 5.55 (1H, m), 1.56 (6H, d, J=6.9 Hz).

EXAMPLE 7

5-isopropyl-3-methylthieno[3,2-b]-3H-imidazo[4,5-d]pyridine-4(5H)-one (Compound 7)

In the same manner as in Example 1, 1.40 g (6.00 mmol) of Compound 6 obtained in Example 6 was used in place of Compound (a) and further the reaction was carried out by the method in Example 2, to obtain 0.81 g (54.6%) of Compound 7.

Melting point: 218.0°–218.8° C.

MS(EI)m/e: 247 (M+).
IR(KBr)cm$^{-1}$: 1630, 1502, 1456, 1237, 864, 772, 730, 623.
NMR (DMSO-d$_6$)δ(ppm): 8.17 (1H, s ), 7.76 (1H, d, J=5.5Hz ), 7.59 (1H, d, J=5.5Hz), 5.48 (1H, m), 4.05 (3H, s), 1.55 (6H, d, J=6.9 Hz).

EXAMPLE 8

3-benzyl-5-isopropylthieno [3,2-b]-3H-imidazo [4,5-d]pyridine-4 (5H)-one (Compound 8)

In the same manner as in Example 3, 0.53 g (2.27 mmol) of Compound 6 obtained in Example 6 was used in place of Compound 1 to obtain 0.37 g (50.4%) of Compound 8.
Melting point: 148°-149° C.
MS(EI)m/e: 323 (M+).
IR(KBr)cm$^{-1}$: 1623, 1574, 1493, 1452, 1367, 1235, 771, 725, 694, 640.
NMR(DMSO-d$_6$)δ(ppm): 8.40 (1H, s), 7.76(1H, d, J=5.4 Hz), 7.59 (1H, d, J=5.4 Hz), 7.26-7.34 (5H, m), 5.73 (2H, s), 5.23-5.64 (1H, br), 1.52 (6H, d, J=6.9 Hz ).

EXAMPLE 9

5-isopropyl-1-methylthieno[3,2-b]-1H-imidazo[4,5-d]pyridine-4(5H)-one (Compound 9)

In the same manner as in Example 4, 1.09 g (4.00 mmol) of Compound (b-4) obtained in the course of synthesis in Reference Example 2 was used in place of Compound (a-4) to obtain 0.51 g (47.8%) of a methylamine derivative of Compound (b). Then, diamino derivative thereof was obtained by the method in Example 1, and formamide was used in place of ethyl orthoformate to obtain 80 mg (17.0%) of Compound 9.
Melting point: 207°-209° C.
MS(EI)m/e: 247 (M+).
IR(KBr cm$^{-1}$: 1643, 1588, 1547, 1251, 1205, 1140, 1103, 854, 780, 638.
NMR(DMSO-d$_6$)δ(ppm): 8.04 (1H, s), 7.91 (1H, d, J=5.4 Hz), 7.66 (1H, d, J=5.4 Hz), 5.26-5.76 (1H, br), 3.96(3H, s), 1.54 (6H, d, J=6.9 Hz)

EXAMPLE 10

1-benzyl-5-isopropylthieno [3,2-b]- 1H-imidazo [4,5 d]pyridine-4 (5H)-one (Compound 10)

In the same manner as in Example 4, 1.09 g (4.00 mmol) of Compound (b-4) obtained in the course of synthesis in Reference Example 2 and benzylamine were used in place of Compound (a-4) and methylamine monohydrochloric acid to obtain 1.09 g (79.6%) of a benzylamino derivative of Compound (b). The reaction was then carried out by the method in Example 1 to obtain 0.69 g (67.2%) of Compound 10.
Melting point: 180°-182° C.
MS (EI)m/e: 323 (M+).
IR(KBr)cm$^{-1}$: 1640, 1585, 1539, 1495, 1452, 1426, 1234, 1208, 1100, 1065, 1031, 781, 741, 720, 694, 676, 647, 606.
NMR(DMSO-d$_6$)δ(ppm): 8.24(1H, s), 7.77(1H, d, J=5.5Hz), 7.57 (1H, d, J=5.5Hz), 7.33 (2H, d, J=7.4 Hz), 7.24-7.37 (1H, m), 7.17 (2H, d, J=7.4 Hz), 5.59(2H, s), 5.21-5.61 (1H, br), 1.59 (6H, d, J=6.9 Hz).

EXAMPLE 11

5-n-propylthieno [3,2-b]-3H- imidazo [4,5-d]pyridine-4(5H)-one (Compound 11)

In the same manner as in Example 1, 1.83 g (7.23 mmol) of Compound (c) obtained in Reference Example 3 was used in place of Compound (a) to obtain 0.84 g (49.8%) of Compound 11.
Melting point: 242.4°-244.6° C.
MS (EI)m/e: 233 (M+).
IR(KBr)cm$^{-1}$: 1651, 1566, 1381, 955, 904, 773, 650.
NMR(DMSO-d$_6$)δ(ppm): 13.57 (1H, br), 8.22 (1H, s), 7.79 (1H, d, J=5.4 Hz), 7.79 (1H, d, J=5.4 Hz), 7.46 (1H, d, J=5.4 Hz), 4.25 (2H, t, J=7.4 Hz), 1.62-1.76 (2H, m), 0.94 (3H, t, J=7.4 Hz)

EXAMPLE 12

3-methyl-5-n-propylthieno [3,2-b]- 3H-imidazo [4,5-d]pyridine-4(5H)-one (Compound 12)

In the same manner as in Example 2, 0.85 g (3.66 mmol) of Compound 11 obtained in Example 11 was used in place of Compound 1 to obtain 0.34 g (37.3%) of Compound 12. Then Compound 12 was stirred with fumaric acid in isopropanol to make a 2-fumarate.
Melting point: 217.4°-221.4° C.
MS(EI)m/e: 247 (M+).
IR(KBr)cm$^{-1}$: 1640, 1500, 1409, 1264, 645.
NMR(DMSO-d$_6$)δ(ppm): 8.15 (1H, s), 7.72 (1H, d, J=5.5Hz), 7.38 (1H, d, J=5.5Hz), 6.63 (4H, s), 4.21 (2H, t, J=7.3Hz), 4.08 (3H, s), 1.63-1.77 (2H, m), 0.95 (3H, t, J=7.3Hz).

EXAMPLE 13

3-benzyl-5-n-propylthieno [3,2-b]-3H-imidazo [4,5-d]pyridine-4(5H)-one (Compound 13)

In the same manner as in Example 3, 1.08 g (4.63 mmol) Compound 11 obtained in Example 11 was used in place of Compound 1 to obtain 0.74 g (49.6%) of Compound 13.
Melting point: 164.3°-165.6° C.
MS(EI) m/e: 323 (M+).
IR(KBrcm$^{-1}$: 1626, 1492, 1455, 1445, 1371, 1242, 1230, 720, 645.
NMR(DMSO-d$_6$)δ(ppm): 8.43 (1H, s), 7.78 (1H, d, J=5.4 Hz ), 7.44 (1H, d, J=5.4 Hz), 7.17-7.37 (5H, m), 5.75 (2H, s), 4.22 (2H, t, J=7.4 Hz), 1.61-1.74 (2H, m), 0.93 (3H, t, J=7.4 Hz).

EXAMPLE 14

1-methyl-5-n-propylthieno [3,2-b]-1H-imidazo [4,5-d]pyridine-4 (5H)-one (Compound 14)

In the same manner as in Example 4, 1.00 g (3.93 mmol) of Compound (c-4) obtained in the course of synthesis in Reference Example 3 was used in place of Compound (a-4) to obtain 0.52 g (49.5%) of a methylamino derivative of Compound (c).

The reaction was then carried out by the method in Example 1 to obtain 0.25 g (55.1%) of Compound 14.
Melting point: 215.9°-216.9 ° C.
MS (EI)m/e: 247 (M+).
IR(KBr)cm$^{-1}$: 1636, 1586, 1399, 1249, 1220, 1066, 780, 729.
NMR(DMSO-d$_6$)δ(ppm): 8.04 (1H, s), 7.91 (1H, d, J=5.4 Hz ), 7.49 (1H, d, J=5.4 Hz), 4.22 (2H, t, J=7.4 Hz ), 3.95 (3H, s), 1.58-1.72 (2H, m), 0.92 (3H, t, J=7.4 Hz )

EXAMPLE 15

1-benzyl-5-n-propylthieno[3,2-b]-1H-imidazo[4,5-d]pyridine-4(5H)-one (Compound 15)

In the same manner as in Example 5, 1.00 g (3.93 mmol) of Compound (c-4) obtained in the course of synthesis in Reference Example 1 was used in place of Compound (a-4) to obtain 0.68 g (50.3%) of a benzylamino derivative of Compound (c).

The reaction was then carried out by the method in Example 1 to obtain 0.23 g (39.4%) of Compound 15.

Melting point: 223.4°–225.0° C.
MS (EI)m/e: 323 (M+).
IR(KBr)cm$^{-1}$: 1642, 1541, 1252, 1064, 781, 726, 648.
NMR(DMSO-d$_6$)δ(ppm): 8.27(1H, s), 7.81 (1H, d, J=5.5Hz), 7.43(1H, d, J=5.5Hz), 7.35(2H, d, J=6.9 Hz), 7.24–7.39 (1H, m), 7.18 (2H, d, J=6.9 Hz), 5.61 (2H, s), 4.21 (2H, t, J=7.4 Hz ), 1.58–1.72 (2H, m), 0.95 (3H, t, J=7.4 Hz).

EXAMPLE 16

5-ethylthieno[3,2-b]-3H-imidazo[4,5-d]pyridine-4(5H)one (Compound 16)

In the same manner as in Example 1, 1.83 g (7.63 mmol) of Compound (d) obtained in Reference Example 4 was used in place of Compound (a) to obtain 0.69 g (41.1%) of Compound 16.

Melting point: 239.6°–241.1° C.
MS(EI)m/e: 219 (M+).
IR(KBr)cm$^{-1}$: 1622, 1599, 1520, 1432, 1235, 772, 648.
NMR(DMSO-d$_6$)δ(ppm): 13.50 (1H, br), 8.15 (1H, s), 7.74 (1H, d, J=5.3Hz), 7.41 (1H, d, J=5.3Hz), 4.34 (2H, q, J=6.9 Hz), 1.28 (3H, t, J=6.9 Hz)

EXAMPLE 17

5-ethyl-3-methylthieno[3,2-b]-3H-imidazo[4,5-d]pyridine-4 (5H)-one (Compound 17)

In the same manner as in Example 2, 0.82 g (3.74 mmol) of Compound 16 obtained in Example 16 was used in place of Compound 1 to obtain 0.20 g (23.4%) of Compound 17.

Melting point: 179.6°–182.0° C.
MS (EI)m/e: 233 (M+).
IR(KBr cm$^{-1}$: 1637, 1504, 1446, 1348, 1290, 1257, 1237, 1045, 770, 729, 621.
NMR (DMSO-d$_6$)δ(ppm ): 8.18(1H, s), 7.78 (1H, d, J=5.3Hz), 7.43 (1H, d, J=5.3Hz), 4.29 (2H, q, J=6.9 Hz), 4.07 (3H, s), 1.25 (3H, t, J=6.9 Hz).

EXAMPLE 18

3-benzyl-5-ethylthieno [3,2-b]-3H-imidazo [4,5-d]pyridine-4(5H)-one (Compound 18)

In the same manner as in Example 3, 0.69 g (3.13 mmol) of Compound 16 obtained in Example 16 was used in place of Compound 1 to obtain 0.34 g (35.3%) of Compound 18.

Melting point: 164.0°–165.0° C.
MS (EI)m/e: 309 (M+).
IR(KBr)cm$^{-1}$: 1637, 1460, 1368, 1239, 849, 733.
NMR(DMSO-d$_6$)δ(ppm): 8.42 (1H, s), 7.79 (1H, d, J=5.4 Hz), 7.44 (1H, d, J=5.4 Hz), 7.25–7.35 (5H, m), 5.75 (2H, s), 4.30 (2H, q, J=6.9 Hz), 1.24 (3H, t, J=6.9 Hz).

EXAMPLE 19

5-ethyl-1-methylthieno [3,2-b]-1H-imidazo [4,5-d]pyridine-4 (5H)-one (Compound 19)

In the same manner as in Example 4, 0.93 g (3.87 mmol) of Compound (d-4) obtained in the course of synthesis in Reference Example 4 was used in place of Compound (a-4) to obtain 0.58 g (59.2%) of a methylamino derivative of Compound (d).

The reaction was then carried out by the method in Example 1 to obtain 0.17 g (31.8%) of Compound 19.

Melting point: 219.0°–220.8° C.
MS (EI)m/e: 233 (M+).
IR(KBr)cm$^{-1}$: 1639, 1546, 1421, 1257, 1224, 1063, 846, 780, 733, 630.
NMR(DMSO-d$_6$)δ(ppm): 8.04 (1H, s), 7.93 (1H, d, J=5.4 Hz), 7.50 (1H, d, J=5.4 Hz), 4.30 (2H, q, J=6.9 Hz), 3.95 (3H, s), 1.21 (3H, t, J=6.9 Hz).

EXAMPLE 20

1-benzyl-5-ethylthieno [3,2-b]-1H-imidazo [4,5-d]pyridine-4 (5H)-one (Compound 20)

In the same manner as in Example 5, 1.50 g (6.63 mmol) of Compound (d-4) obtained in the course of synthesis in Reference Example 4 was used in place of Compound (a-4) to obtain 0.88 g (40.3%) of a benzylamino derivative of Compound (d).

The reaction was then carried out by the method in Example 1 to obtain 0.58 g (70.2%) of Compound 20.

Melting point: 188.4°–189.4° C.
MS(EI)m/e: 309 (M+).
IR(KBr) cm$^{-1}$: 1662, 1574, 1545, 1454, 1257, 1228, 1057, 730, 646.
NMR(DMSO-d$_6$)δ(ppm): 8.33 (1H, s), 7.82 (1H, d, J=5.5Hz ), 7.42 (1H, d, J=5.5Hz), 7.17–7.39 (5H, m), 5.61 (2H, s), 4.29 (2H, q, J=6.9 Hz), 1.21 (3H, t, J=6.9 Hz).

EXAMPLE 21

5-methylthieno[3,2-b]-3H-imidazo[4,5-d]pyridine-4(5H)-one (Compound 21)

In the same manner as in Example 1, 2.90 g (12.88 mmol) of Compound (e) obtained in Reference Example 5 was used in place of Compound (a) to obtain 1.20 g (45.3%) of Compound 21.

MS (EI)m/e: 205 (M+).
NMR(DMSO-d$_6$)δ(ppm): 13.56(1H, br), 8.19(1H, s), 7.77 (1H, d, J=5.4 Hz), 7.41 (1H, d, J=5.4 Hz), 3.74 (3H, s).

EXAMPLE 22

3,5-dimethylthieno [3,2-b]-3H-imidazo [4,5-d]pyridine-4 (5H)-one (Compound 22)

In the same manner as in Example 2, 0.63 g (3.09 mmol) of Compound 21 obtained in Example 21 was used in place of Compound 1 to obtain 0.30 g (44.9%) of Compound 22.

MS(EI)m/e: 219 (M+).
NMR(DMSO-d$_6$)δ(ppm): 8.17 (1H, s), 7.76(1H, d, J=5.4 Hz), 7.39 (1H, d, J=5.4 Hz), 4.06 (3H, s), 3.69 (3H, s)

EXAMPLE 23

3-benzyl-5-methylthieno [3,2-b]-3H-imidazo [4,5-d]pyridine-4 (5H)-one (Compound 23)

In the same manner as in Example 3, 0.50 g (2.44 mmol) of Compound 21 obtained in Example 21 was used in place of Compound 1 to obtain 0.15 g (21.5%) of Compound 23.

MS(EI)m/e: 295 (M+).
NMR(DMSO-d$_6$)δ(ppm): 8.43 (1H, s), 7.78 (1H, d, J=5.4 Hz), 7.40 (1H, d, J=5.4 Hz), 7.23–7.34(5H, m), 5.75 (2H, s), 3.70 (3H, s)

EXAMPLE 24

1,5-dimethylthieno [3,2-b]-1H-imidazo [4,5-d]pyridine-4(5H)-one (Compound 24)

In the same manner as in Example 4, 1.64 g (7.23 mmol) of Compound (e-4) obtained in the course of synthesis in Reference Example 5 was used in place of Compound (a-4) to obtain 0.51 g (29.7%) of a methylamino derivative of Compound (e).

The reaction was then carried out by the method in Example 1 to obtain 0.89 g (91.2%) of Compound 24.

MS(EI)m/e: 219 (M+).
NMR(DMSO-d$_6$)δ(ppm): 8.03 (1H, s), 7.90 (1H, d, J=5.4 Hz), 7.44 (1H, d, J=5.4 Hz), 3.95 (3H, s), 3.69 (3H, s).

EXAMPLE 25

1-benzyl-5-methylthieno [3,2-b]-1H-imidazo [4,5-d]pyridine-4(5H)-one (Compound 25)

In the same manner as in Example 5, 1.36 g (6.01 mmol) of Compound (e-4) obtained in the course of synthesis in Reference Example 5 was used in place of Compound (a-4) to obtain 1.07 g (56.6%) of a benzylamino derivative of Compound (e).

The reaction was then carried out by the method in Example 1 to obtain 0.84 g (89.2%) of Compound 25.

MS(EI)m/e: 295 (M+).
NMR(DMSO-d$_6$)δ(ppm): 8.27 (1H, s), 7.81 (1H, d, J=5.4 Hz), 7.26–7.51 (4H, m), 7.16 (2H, d, J=6.4 Hz), 5.62 (2H, s), 3.69 (3H, s)

EXAMPLE 26

5-isobutylthieno [3,2-b]-3H-imidazo [4,5-d]pyridine-(5H)-one (Compound 26)

In the same manner as in Example 1, 1.37 g (5.13 mmol) of Compound (f) obtained in Reference Example 6 was used in place of Compound (a) to obtain 0.97 g (76.2%) of Compound 26.

Melting point: 291.1°–294.0° C.
MS (EI)m/e: 247 (M+).
IR(KBr)cm$^{-1}$: 1640, 1378, 1266, 1231, 1102, 774, 722.
NMR(DMSO-d$_6$)δ(ppm): 13.53 (1H, br), 8.19 (1H, s), 7.75 (1H, d, J=5.5Hz), 7.42 (1H, d, J=5.5Hz), 4.14 (2H, d, J=7.6Hz), 2.09–2.26 (1H, m), 0.91 (6H, d, J=6.9 Hz).

EXAMPLE 27

5-isobutyl-3-methylthieno [3,2-b ]-3H-imidazo [4,5-d]pyridine-4(5H)-one (Compound 27)

In the same manner as in Example 2, 0.38 g (1.52 mmol) of Compound 26 obtained in Example 26 was used in place of Compound 1 to obtain 0.33 g (82.3%) of Compound 27. Then Compound 27 was stirred with fumaric acid in isopropanol to make a fumarate.

Melting point: 195.6°–196.0° C.
MS(EI)m/e: 261 (M+).
IR(KBr)cm$^{-1}$: 1642, 1278, 1215, 1048, 769.
NMR(DMSO-d$_6$)δ(ppm): 8.18 (1H, s), 7.75 (1H, d, J=5.4 Hz), 7.41 (1H, d, J=5.4 Hz), 6.63 (2H, s), 4.08 (2H, d, J=7.4 Hz), 4.06 (3H, s), 2.10–2.20 (1H, m), 0.91 (6H, d, J=6.4 Hz)

EXAMPLE 28

3-benzyl-5-isobutylthieno [3,2-b]-3H-imidazo [4,5-d]pyridine-4 (SH)-one (Compound 28)

In the same manner as in Example 3, 0.85 g (3.42 mmol) of Compound 26 obtained in Example 26 was used in place of Compound 1 to obtain 0.42 g (36.4%) of Compound 28. Then, Compound 28 was stirred with fumaric acid in isopropanol to make a fumarate.

Melting point: 171.7°–172.2° C.
MS(EI)m/e: 337 (M+).
IR(KBr) cm$^{-1}$: 1677, 1654, 1424, 1278, 1228, 726, 697, 648.
NMR (DMSO-d$_6$)δ(ppm): 13.09 (2H, br), 8.43 (1H, s), 7.76(1H, d, J=5.3Hz), 7.32 (1H, d, J=5.3HZ), 7.24–7.43 (5H, m), 6.63 (2H, s), 5.74 (2H, S). 4.11 (2H, d, J=7.3Hz), 2.05–2.20 (1H, m), 0.89 (6H, d, J=6.6Hz)

EXAMPLE 29

5-isobutyl-1-methylthieno[3,2-b]-1H-imidazo[4,5-d]pyridine-4(5H)-one (Compound 29)

In the same manner as in Example 4, 2.13 g (7.94 mmol) of Compound (f-4) obtained in the course of synthesis in Reference Example 6 was used in place of Compound (a-4) to obtain 1.79 g (80.0%) of a methylamino derivative of Compound (f).

The reaction was then carried out by the method in Example 1 to obtain 0.51 g (30.6%) of Compound 29.

Melting point: 198.8°–200.9° C.
MS(EI)m/e: 261 (M+).
IR(KBr) cm$^{-1}$: 1658, 1645, 1250, 1068, 667.
NMR(DMSO-d$_6$)δ(ppm): 8.04 (1H, s), 7.88 (1H, d, J=5.4 Hz), 7.46 (1H, d, J=5.4 Hz), 4.12 (2H, d, J=7.4 Hz), 3.97 (3H, s), 2.05–2.20(1H, m), 0.88 (6H, d, J=6.9 Hz)

EXAMPLE 30

1-benzyl-5-isobutylthieno [3,2-b]-1H-imidazo [4,5-d]pyridine-4 (5H)-one (Compound 30)

In the same manner as in Example 5, 0.81 g (3.00 mmol) of Compound (f-4) obtained in the course of synthesis in Reference Example 6 was used in place of Compound (a-4) to obtain 0.66 g (62.0%) of a benzylamino derivative of Compound (f).

The reaction was then carried out by the method in Example 1 to obtain 0.53 g (68.1%) of Compound 30.

Melting point: 184.1°–185.8° C.
MS (EI)m/e: 337 (M+).
IR(KBr) cm$^{-1}$: 1640, 1248, 1223, 1069, 780, 728.
NMR(DMSO-d$_6$)δ(ppm): 8.26 (1H, s), 7.78 (1H, d, J=5.6Hz),
7.26–7.41 (5H, m), 7.19 (1H, d, J=5.6Hz), 5.61 (2H, s), 4.11 (2H, d, J=7.6Hz), 2.02–2.19 (1H, m), 0.89 (6H, d, J=6.6Hz)

EXAMPLE 31

5-n-butylthieno [2,3-b]-3H-imidazo [4,5-d]pyridine-4 (5H) one (Compound 31)

In the same manner as in Example 1, 1.12 g (4.18 mmol) of Compound (g) obtained in Reference Example 7 was used in place of Compound (a) to obtain 0.47 g (47.8%) of Compound 31.

Melting point: 251.8°–254.9° C.
MS(EI)m/e: 247 (M+).
IR(KBr)cm$^{-1}$: 1650, 1614, 1535, 1270, 1237, 1208, 1125, 959, 647.
NMR(DMSO-d$_6$)δ(ppm): 13.27(1H, br), 8.15 (1H, s), 7.46 (1H, d, J=5.4 Hz), 7.37 (1H, d, J=5.4 Hz), 4.14 (2H, t, J=7.4 Hz), 1.66–1.97 (2H, m), 1.30–1.43 (2H, m), 0.89 (3H, t, J=7.4 Hz).

EXAMPLE 32

5-n-butyl-3-methylthieno [2,3-b]-3H-imidazo [4,5-d]pyridine-4 (5H)-one (Compound 32)

In the same manner as in Example 2, 0.88 g (3.56 mmol) of Compound 31 obtained in Example 31 was used in place of Compound 1 to obtain 0.39 g (41.9%) of Compound 32.

Melting point: 102.8°–105.6° C.
MS(EI)m/e: 261 (M+).
IR(KBr) cm$^{-1}$: 1645, 1586, 1506, 1466, 1456, 1284, 1232, 1205, 1171, 1122, 735, 614.
NMR (DMSO-d$_6$)δ(ppm): 8.18 (1H, s), 7.46 (1H, d, J=5.4 Hz), 7.37 (1H, d, J=5.4 Hz), 4.13 (2H, t, J=7.4 Hz), 4.06 (3H, s), 1.65–1.79 (2H, m), 1.32–1.46 (2H, m), 0.92 (3H, t, J=7.4 Hz).

EXAMPLE 33

3-benzyl-5-n-butylthieno [2,3-b]-3H-imidazo [4,5-d]pyridine-4 (5H)-one (Compound 33)

In the same manner as in Example 3, 1.00 g (4.04 mmol) of Compound 31 obtained in Example 31 was used in place of Compound 1 to obtain 0.70 g (51.3%) of Compound 33.

Melting point: 96.0°–98.9° C.
MS(EI)m/e: 337 (M+).
IR(KBr) cm$^{-1}$: 1659, 1584, 1493, 1456, 1239, 1210, 1174, 722, 690, 623.
NMR(DMSO-d$_6$)δ(ppm): 8.20 (1H, s), 7.19–7.37 (5H, m), 7.14 (2H, d, J=6.9 Hz), 5.77 (2H, s), 4.12 (2H, t, J=7.4 Hz), 1.64–1.75 (2H, m), 1.29–1.43 (2H, m), 0.92 (3H, t, J=7.4 Hz)

EXAMPLE 34

5-n-butyl-1-methylthieno [2,3-b]-1H-imidazo [4,5-d]pyridine-4 (5H)-one (Compound 34)

In the same manner as in Example 4, 2.00 g (7.45 mmol) of Compound (g-4) obtained in the course of synthesis in Reference Example 7 was used in place of Compound (a-4) to obtain 0.45 g (21.5%) of a methylamino derivative of Compound (g).

The reaction was then carried out by the method in Example 1 to obtain 0.23 g (49.5%) of Compound 34. Then, Compound 34 was stirred with fumaric acid in isopropanol to yield 0.6 g of a fumarate.

Melting point: 172.7°–173.9° C.
MS (EI)m/e: 261 (M+).
IR(KBr) cm$^{-1}$: 1689, 1653, 1502, 1277, 1244, 1220, 1201, 1127, 1054, 778, 739, 713, 641.
NMR(DMSO-d$_6$)δ(ppm): 8.00(1H, s), 7.65(1H, d, J=5.5Hz), 7.45 (1H, d, J=5.5Hz), 6.63 (1.2H, s), 4.15 (2H, t, J=7.4 Hz), 4.03 (3H, s), 1.66–1.77 (2H, m), 1.31–1.45 (2H, m), 0.92 (3H, t, J=7.4 Hz)

EXAMPLE 35

1-benzyl-5-n-butylthieno [2,3-b]-1H-imidazo [4,5-d]pyridine-4 (5H)-one (Compound 35)

In the same manner as in Example 5, 2.10 g (7.50 mmol) of Compound (g-4) obtained in the course of synthesis in Reference Example 7 was used in place of Compound (a-4) to obtain 1.52 g (56.8%) of a benzylamino derivative of Compound (g).

The reaction was then carried out by the method in Example 1 to obtain 1.06 g (73.8%) of Compound 35.

Melting point: 127.3°–134.5° C.
MS(EI)m/e: 337 (M+).
IR(KBr) cm$^{-1}$: 1641, 1501, 1454, 1245, 718, 652.
NMR(DMSO-d$_6$)δ(ppm): 8.24 (1H, s), 7.16–7.39 (5H, m), 7.18 (2H, d, J=4.9 Hz), 5.74 (2H, s), 4.14 (2H, t, J=7.4 Hz), 1.66–1.77 (2H, m), 1.31–1.45 (2H, m), 0.92 (3H, t, J=7.4 Hz).

EXAMPLE 36

5-n-propylthieno[2,3-b]-3H-imidazo [4,5-d]pyridine-4(5H)-one (Compound 36)

In the same manner as in Example 1, 3.17 g (12.52 mmol) of Compound (h) obtained in Reference Example 8 was used in place of Compound (a) to obtain 0.82 g (28.2%) of Compound 36.

Melting point: 166.1°–166.5° C.
MS(EI)m/e: 233 (M+).
IR(KBr)cm$^{-1}$: 1659, 1536, 1271, 1246, 1221, 1184, 1122, 779, 647.
NMR(DMSO-d$_6$)δ(ppm): 8.17 (1H, s), 7.48 (1H, d, J=5.6Hz), 7.39 (1H, d, J=5.6Hz), 4.13 (2H, t, J=7.6Hz), 1.72–1.86 (2H, m), 0.95 (3H, t, J=7.6Hz).

EXAMPLE 37

3-methyl-5-n-propylthieno[2,3-b]-3H-imidazo[4,5-d]pyridine-4 (5H)-one (Compound 37)

In the same manner as in Example 2, 1.18 g (5.06 mmol) of Compound 36 obtained in Example 36 was used in place of Compound 1 to obtain 0.67 g (53.4%) of Compound 37. Then, Compound 37 was stirred with fumaric acid in isopropanol to yield 0.7 g of a fumarate.

Melting point: 226.3°–227.2° C.
MS (EI)m/e: 247 (M+).
IR(KBr)cm$^{-1}$: 1650, 1506, 1468, 1360, 1266, 1213, 1173, 992, 787, 730, 620.
NMR(DMSO-d$_6$)δ(ppm): 8.17 (1H, s), 7.46 (1H, d, J=5.4 Hz), 7.37 (1H, d, J=5.4 Hz), 6.63 (1.4 H, s), 4.10 (2H, t, J=7.4 Hz), 4.06 (3H, s), 1.72–1.86 (2H, m), 0.96 (3H, t, J=7.4 Hz).

EXAMPLE 38

3-benzyl-5-n-propylthieno[2,3-b]-3H-imidazo [4,5-d]pyridine-4 (5H)-one (Compound 38)

In the same manner as in Example 3, 0.45 g (1.92 mmol) of Compound 36 obtained in Example 36 was used in place of Compound 1 to obtain 0.51 g (81.2%) of Compound 38.

Melting point: 263.0°–264.7° C.
MS (EI)m/e: 323 (M+).
IR(KBr) cm$^{-1}$: 1640, 1503, 1241, 1221, 730, 699.
NMR(DMSO-d$_6$)δ(ppm): 8.41 (1H, s), 7.47 (1H, d, J=5.4 Hz), 7.37(1H, d, J=5.4 Hz), 7.15–7.34 (5H, m), 5.73 (2H, s), 4.11 (2H, t, J=7.4 Hz), 1.71–1.85 (2H, m), 0.95 (3H, t, J=7.4 Hz)

EXAMPLE 39

1-benzyl-5-n-propylthieno [2,3-b]-1H-imidazo [4,5-d]pyridine-4 (5H)-one (Compound 39)

In the same manner as in Example 5, 1.40 g (5.51 mmol) of Compound (h-4) obtained in the course of synthesis in Reference Example 8 was used in place of Compound (a-4) to obtain 1.48 g (78.2%) of a benzylamino derivative of Compound (h).

The reaction was then carried out by the method in Example 1 to obtain 0.47 g (35.3%) of Compound 39.

Melting point: 155.0°–157.6° C.

MS (EI)m/e: 323 (M+).

IR(KBr)cm$^{-1}$: 1640, 1540, 1500, 1455, 1249, 1218, 1121, 731, 652.

NMR(DMSO-d$_6$)δ(ppm): 8.23(1H, s), 7.06–7.38 (5H, m), 7.16 (2H, d, J=6.9 Hz), 5.73 (2H, s), 4.10 (2H, t, J=7.4 Hz), 1.68–1.82 (2H, m), 0.94 (3H, t, J=7.4 Hz).

EXAMPLE 40

Tablets

Tablets, each having the following composition, are prepared in a conventional manner.

Compound 1 10 mg
Lactose 30 mg
Potato starch 15 mg
Polyvinyl alcohol 1.5 mg
Magnesium stearate 0.5 mg

EXAMPLE 41

Capsules

Capsules, each having the following composition, are prepared in a conventional manner.

Compound 1 10 mg
Lactose 100 mg
Magnesium stearate 2.5 mg

These components are mixed together and filled into a gelatin capsule.

EXAMPLE 42

Injection

Injection, having the following composition, is prepared in a conventional manner.

Compound 1 10 mg
Sodium chloride 20 mg

The composition is added to water to make the total volume 5 ml (for 1 ampule). The water is distilled in advance and sterilized in an autoclave.

EXAMPLE 43

Powder

Powder, having the following composition, is prepared in a conventional manner.

Compound 1 10 mg
Lactose 150 mg

EXAMPLE 44

Syrup

Syrup, having the following composition, is prepared in a conventional manner.

Compound 1 10 mg
Refined sucrose 15 mg
Ethyl p-hydroxy benzoate 20 mg
Propyl p-hydroxy benzoate 5 mg
Strawberry flavor 0.05 cc Water is added to the composition to make the total volume 50 cc.

REFERENCE EXAMPLE 1

7-amino-4-n-butyl-6-nitrothieno [3,2-b]pyridine-5(4H)one [Compound (a)]

1) Methyl 3-mono-n-butylaminothiophene-2-carboxylate [Compound (a-1)]

To 200 ml of an N,N-dimethylformamide solution containing 15.7 g (0.100 mol) of methyl 3-aminothiophene-2-carboxylate and 15.2 g (0.110 mol) of potassium carbonate was added 34.1 ml (0.300 tool) of n-butyl iodide at 25° C., and the mixture was stirred at 120° C. for 10 hours. After cooling, the solvent was distilled off under reduced pressure, and 200 ml of ethyl acetate was added thereto, and then the inorganic salt was filtered off. The filtrate was concentrated also under reduced pressure. The resulting residue was purified by silica gel column chromatography to obtain 10.2 g (48%) of Compound (a-1).

NMR(CDCl$_3$)δ(ppm): 7.35 (1H, d, J=5.3Hz), 7.01–7.30 (1H, br), 6.9 8(1H, d, J=5.3Hz), 3.83 (3H, s), 3.28 (2H, m), 1.21–1.88 (4H, m), 0.95 (3H, t, J=7.5Hz)

2) 4-n-butyl-5H-thieno[3,2-d]oxadine-5,7(4H)-dione [Compound (a-2)]

To a solution of 10.0 g (46.9 mmol) of Compound (a-1) in a mixture of 90 ml of 1,2-dichloroethane and 9 ml of 1,4-dioxane was added dropwise 16.9 ml (0.141 mol) of trichloromethyl chloroformate at 25° C. The mixture was stirred at 75° C. for 7 hours. After cooling, 0.50 g of active carbon was added thereto, and the mixture was refluxed under a nitrogen atmosphere for 1 hour. After cooling, the active carbon was filtered off, and the filtrate was concentrated under reduced pressure. To the resulting residue were added 15 ml of ethyl acetate and 50 ml of n-hexane, and the mixture was stirred. The precipitated white crystals were taken by filtration and dried to obtain 6.96 g (66%) of Compound (a-2).

NMR(DMSO-d$_6$)δ(ppm): 8.33 (1H, d, J=5.4 Hz), 7.38 (1H, d, J=5.4 Hz), 3.94(2H, t, J=7.4 Hz), 1.57–1.68 (2H, m), 1.29–1.43 (2H, m), 0.90 (3H, t, J=7.4 Hz).

4-n-butyl-7-hydroxy-6-nitrothieno [3,2-b]pyridine-5 (4H)-one [Compound (a-3)]

To dimethylacetamide (DMA; 75 ml) containing 5.00 ml (45.2 mmol) of ethyl nitroacetate was added 1.08 g (45.2 mmol) of sodium hydride. The mixture was stirred at 25° C. for 30 minutes. Then, 8.15 g (36.2 mmol) of Compound (a-2) was added thereto, and the mixture was washed with chloroform. Then, in aqueous hydrochloric acid was added thereto for acidification, and the resulting brown crystals were taken by filtration to obtain 8.10 g (83.4%) of Compound (a-3).

NMR(DMSO-d$_6$)δ(ppm): 8.18 (1H, d, J=5.4 Hz), 7.43 (1H, d, J=5.4 Hz), 4.13 (2H, t, J=7.4 Hz), 1.53–1.64 (2H, m), 1.27–1.40 (2H, m), 0.90 (3H, t, J=7.4 Hz)

4) 4-n-butyl-7-chloro-6-nitrothieno [3,2-b]pyridine-5 (4H)-one [Compound (a-4)]

To 3.87 g (14.4 mmol) of Compound (a-3) was added 35 ml of phosphorous oxychloride, and the mixture was refluxed for 1 hour. After cooling, the phosphorus oxychloride was distilled off. Then 1N aqueous sodium hydroxide was added thereto, and the mixture was extracted with chloroform. The extract was dried over anhydrous sodium sulfate and concentrated. The resulting residue was purified by column chromatography to obtain 3.87 g (42.3%) of Compound (a-4) as brown crystals.

5) 7-amino-4-n-butyl-6-nitrothieno [3,2-b]pyridine-5 (4H)-one [Compound (a)]

To a dry tetrahydrofuran (THF; 70 ml) solution containing 2.24 g (7.81 mmol) of Compound (a-4) was added 14 ml of a 29% aqueous ammonia. The mixture was stirred at 25° C. for 8 hours. The mixed solution was added to water, and extracted with chloroform. Then, the extract was dried over anhydrous sodium sulfate to obtain 2.05 g (98.3%) of Compound (a) as brown crystals.

NMR(DMSO-$d_6$)$\delta$(ppm): 8.17 (2H, s), 8.16 (1H, d, J=5.4 Hz), 7.34 (1H, d, J=5.4 Hz), 4.07 (2H, t, J=7.4 Hz), 1.50–1.62 (2H, m), 1.26–1.37 (2H, m), 0.90 (3H, t, J=7.4 Hz)

REFERENCE EXAMPLE 2

7-amino-4-isopropyl-6-nitrothieno[3,2-b]pyridine-5(4H)-one [Compound (b)]

1) Methyl 3-mono-isopropylaminothiophene-2-carboxylate [Compound (b-1)]

In the same manner as in Reference Example 1-1), 25.0 g (0.159 mmol) of isopropyl iodide was used in place of n-butyl iodide to obtain 11.2 g (35.3%) of Compound (b-1).

NMR(CDCl$_3$)$\delta$(ppm): 7.30 (1H, d, J=5.3Hz), 6.62 (1H, d, J=5.3Hz), 6.50–6.81 (1H, br), 3.79 (3H, s), 3.68 (1H, m), 1.17 (6H, d, J=6.2Hz).

2) 4-isopropyl-5H-thieno [3,2-d]oxadine-5,7 (4H)-dione [Compound (b-2)]

In the same manner as in Reference Example 1-2), 12.6 g (59.1 mmol) of Compound (b-1) was used in place of Compound (a-1) to obtain 12.5 g (93.6%) of Compound (b-2).

NMR(DMSO-$d_6$)$\delta$(ppm): 8.32 (1H, d, J=5.4 Hz), 7.50 (1H, d, J=5.4 Hz), 4.74 (1H, m), 1.46 (6H, d, J=6.9 Hz).

3) 7-hydroxy-4-isopropyl-6-nitrothieno [3,2-b]pyridine-5(4H)-one [Compound (b-3)]

In the same manner as in Reference Example 1-3), 12.4 g (55.0 mmol) of Compound (b-2) was used in place of Compound (a-2) to obtain 10.6 g (71.0%) of Compound (b-3).

NMR(DMSO-$d_6$)$\delta$(ppm): 8.16 (1H, d, J=5.4 Hz), 7.59 (1H, d, J=5.4Hz), 5.23 (1H, br ), 1.49 (6H, d, J=6.9 Hz)

4) 7-chloro-4-isopropyl-6-nitrothieno[3,2-b]pyridine-5(4H)-one [Compound (b-4)]

In the same manner as in Reference Example 1-4), 5.80 g (22.8 mmol) of Compound (b-3) was used in place of Compound (a-3) to obtain 2.44 g (39.2%) of Compound (b-4).

5) 7-amino-4-isopropyl-6-nitrothieno [3,2-b]pyridine-5 (4H)-one [Compound (b )]

In the same manner as in Reference Example 1-5), 2.44 g (22.8 mmol) of Compound (b-4) was used in place of Compound (a-4) to obtain 2.02 g (89.1%) of Compound (b).

NMR(DMSO-$d_6$)$\delta$(ppm): 8.14 (1H, d, J=5.9 Hz), 8.03 (2H, s), 7.51 (1H, d, J=5.9 Hz), 5.18 (1H, br), 1.46 (6H, d, J=6.9 Hz).

REFERENCE EXAMPLE 3

7-amino-6-nitro-4-n-propylthieno[3,2-b]pyridine-5 (4H) one [Compound (c)]

1) Methyl 3-mono-n-propylaminothiophene-2-carboxylate [Compound (c-1)]

In the same manner as in Reference Example 1-1), 2.63 g (0.155 mmol) of n-propyl iodide was used in place of n-butyl iodide to obtain 8.86 g (44.5%) of Compound (c-1).

NMR (CDCl$_3$)$\delta$(ppm): 7.32 (1H, d, J=5.4 Hz), 6.63 (1H, d, J=5.4 Hz), 3.81 (3H, s), 3.23 (2H, t, J=6.9 Hz), 1.58–1.69 (2H, m), 0.99 (3H, t, J=7.4 Hz)

4-n-propyl-5H-thieno [3,2-d]oxadine-5,7 (4H)-dione [Compound (c -2)]

In the same manner as in Reference Example 1-2), 23.41 g (117.5 mmol) of Compound (c-1) was used in place of Compound (a-1) to obtain 15.02 g (60.5%) of Compound (c-2).

NMR(DMSO-$d_6$)$\delta$(ppm): 8.33 (1H, d, J=5.4 Hz), 7.41 (1H, d, J=5.4 Hz), 3.91 (2H, t, J=7.4 Hz), 1.57–1.79 (2H, m), 0.92 (3H, t, J=7.4 Hz).

3) 7-hydroxy-6-nitro-4-n-propylthieno[3,2-b]pyridine-5(4H)-one [Compound (c-3)]

In the same manner as in Reference Example 1-3), 6.34 g (30.0 mmol) of Compound (c-2) was used in place of Compound (a-2) to obtain 4.48 g (58.7%) of Compound (c-3).

NMR(DMSO-$d_6$)$\delta$(ppm): 8.19 (1H, d, J=5.4 Hz), 7.46 (1H, d, J=5.4 Hz), 4.10 (2H, t, J=7.4 Hz), 1.57–1.70 (2H, m), 0.90 (3H, t, J=7.4 Hz)

4) 7-amino-6-nitro-4-n-propylthieno [3,2-b]pyridine-5(4H) one [Compound (c)]

In the same manner as in Reference Examples 1-4) and 1-5), 4.85 g (19.07 mmol) of Compound (c-3) was used in place of Compound (a-3) to obtain 3.03 g (62.7%) of Compound (c).

NMR(DMSO-$d_6$)$\delta$(ppm): 7.77 (1H, d, J=5.4 Hz), 7.03 (1H, d, J=5.4 Hz), 7.00 (2H, br), 4.12 (2H, t, J=6.4Hz), 1.64–1.85 (2H, m), 1.01 (3H, t, J=6.4Hz).

REFERENCE EXAMPLE 4

7-amino-4-ethyl-6-nitrothieno[3,2-b]pyridine-5(4H)-one [Compound (d)]

Methyl 3-mono-ethylaminothiophene-2-carboxylate Compound (d-1)]

In the same manner as in Reference Example 1-1), 37.20 (238.5 mmol) of ethyl iodide was used in place of n-butyl iodide to obtain 20.30 g (68.9%) of Compound (d-1).

2) 4-ethyl-5H-thieno[3,2-d]oxadine-5,7(4H)-dione [Compound (d-2)]

In the same manner as in Reference Example 1-2), 20.30 (110.0 mmol) of Compound (d-1) was used in place of Compound (a-1) to obtain 12.55 g (58.1%) of Compound (d-2).

NMR(DMSO-$d_6$)δ(ppm): 8.35 (1H, d, J=5.4 Hz), 7.41(1H, d, J=5.4 Hz), 3.99 (2H, q, J=6.9 Hz), 1.22 (3H, t, J=6.9 Hz)

3) 4-ethyl-7-hydroxy-6-nitrothieno[3,2-b]pyridine-5(4H) one [Compound (d-3)]

In the same manner as in Reference Example 1-3), 3.94 g (20.0 mmol) of Compound (d-2) was used in place of Compound (a-2) to obtain 3.30 g (68.8%) of Compound (d-3).

NMR(DMSO-$d_6$)δ(ppm): 8.21 (1H, d, J=5.4 Hz), 7.47 (1H, d, J=5.4 Hz), 4.21 (2H, q, J=6.9 Hz), 1.20 (3H, t, J=6.9 Hz).

4) 7-amino-4-ethyl-6-nitrothieno[3,2-b]pyridine-5(4H)-one [Compound (d)]

In the same manner as in Reference Examples 1-4) and 1-5), 4.04 g (16.82 mmol) of Compound (d-3) was used in place of Compound (a-3) to obtain 1.97 g (49.0%) of Compound (d).

NMR(DMSO-$d_6$)δ(ppm): 8.19 (2H, s), 8.16 (1H, d, J=5.4 Hz), 7.34(1H, d, J=5.4 Hz), 4.12(2H, q, J=6.9 Hz), 1.18 (3H, t, J=6.9 Hz)

REFERENCE EXAMPLE 5

7-amino-4-methyl-6-nitro thieno[3,2-b]pyridine-5(4H)-one [Compound (e)]

1) Methyl 3-mono-methylaminothiophene-2-carboxylate [Compound (e-1)]

In the same manner as in Reference Example 1-1), 33.86 (238.5 mmol) of methyl iodide was used in place of n-butyl iodide to obtain 12.99 g (47.7%) of Compound (e-1).

NMR (CDCl$_3$)δ(ppm): 7.18 (1H, d, J=5.3Hz), 6.45 (1H, d, J=5.3 Hz), 6.34–6.70 (1H, br), 3.69 (3H, s), 3.21 (3H, s)

2) 4-methyl-5H-thieno[3,2-d]oxadine-5,7(4H)-dione [Compound (e-2)]

In the same manner as in Reference Example 1-2), 6.56 g (38.3 mmol) of Compound (e-1) was used in place of Compound (a-1) to obtain 5.77 g (82.2%) of Compound (e-2).

NMR(DMSO-$d_6$)δ(ppm): 8.33 (1H, d, J=5.4 Hz), 7.34 (1H, d, J=5.4 Hz), 3.45 (3H, s)

3) 7-hydroxy-4-methyl-6-nitrothieno[3,2-b]pyridine-5(4H)one [Compound (e-3)]

In the same manner as in Reference Example 1-3), 5.76 g (31.4 mmol) of Compound (e-2) was used in place of Compound (a-2) to obtain 4.69 g (66.0%) of Compound (e-3).

NMR(DMSO-$d_6$)δ(ppm): 8.17 (1H, d, J=5.4 Hz), 7.40 (1H, d, J=5.4 Hz), 3.59 (3H, s).

4) 7-amino-4-methyl-6-nitrothieno[3,2-b]pyridine-5(4H)-one [Compound (e)]

In the same manner as in Reference Examples 1-4) and 1-5), 5.52 g (24.4 mmol) of Compound (e-3) was used in place of Compound (a-3) to obtain 1.88 g (34.2%) of Compound (e).

NMR(DMSO-$d_6$)δ(ppm): 8.21 (2H, s), 8.15 (1H, d, J=5.4 Hz), 7.31 (1H, d, J=5.4 Hz), 3.52 (3H, s).

REFERENCE EXAMPLE 6

7-amino-4-isobutyl-6-nitrothieno[3,2-b]pyridine-5(4H) one [Compound (f)]

1) Methyl 3-mono-isobutylaminothiophene-2-carboxylate [Compound (f-1)]

In the same manner as in Reference Example 1-1), 43.90 g (238.5 mmol) of isobutyl iodide was used in place of n-butyl iodide to obtain 16.92 g (49.9%) of Compound (f-1).

NMR(CDCl$_3$)δ(ppm): 7.31 (1H, d, J=5.4 Hz), 6.89 (1H, br), 6.62 (1H, d, J=5.4 Hz), 3.81 (3H, s), 3.08 (2H, t, J=6.4Hz), 1.78–1.95 (1H, m), 0.98 (6H, d, J=6.4Hz).

2) 4-isobutyl-5H-thieno[3,2-d]oxadine-5,7(4H)-dione Compound (f-2)]

In the same manner as in Reference Example 1-2), 10.64 g (49.9 mmol) of Compound (f-1) was used in place of Compound (a-1) to obtain 9.54 g (84.9%) of Compound (f-2).

NMR(DMSO-$d_6$)δ(ppm): 8.32 (1H, d, J=5.4 Hz), 7.41 (1H, d, J=5.4 Hz), 3.78 (2H, d, J=7.4 Hz), 1.97–2.15 (1H, m), 0.92 (6H, d, J=6.4Hz)

3) 7-hydroxy-4-isobutyl-6-nitrothieno[3,2-b]pyridine-5(4H)-one [Compound (f-3)]

In the same manner as in Reference Example 1-3), 9.54 g (42.4 mmol) of Compound (f-2) was used in place of Compound (a-2) to obtain 7.93 g (69.8%) of Compound (f-3).

NMR(DMSO-$d_6$)δ(ppm): 8.17 (1H, d, J=5.4 Hz), 7.44(1H, d, J=5.4 Hz), 3.99 (2H, d, J=7.4 Hz), 2.02–2.17 (1H, m), 0.89 (6H, d, J=6.9 Hz)

4) 7-amino-4-isobutyl-6-nitrothieno[3,2-b]pyridine-5(4H) one [Compound (f)]

In the same manner as in Reference Examples 1-4) and 1-5), 4.02 g (15.0 mmol) of Compound (f-3) was used in place of Compound (a-3) to obtain 2.09 g (52.2%) of Compound (f).

NMR(DMSO-$d_6$)δ(ppm): 8.18 (2H, s), 8.13 (1H, d, J=5.4 Hz), 7.34(1H, d, J=5.4 Hz), 3.92(2H, d, J=7.4 Hz), 1.98–2.13 (1H, m), 0.88 (6H, d, J=6.9 Hz).

REFERENCE EXAMPLE 7

4-amino-7-n-butyl-5-nitrothieno[2,3-b]pyridine-6(7H)-one [Compound (g)]

1) Methyl 2-mono-n-butylaminothiophene-3-carboxylate [Compound (g-1)]

In the same manner as in Reference Example 1-1), methyl 2-aminothiophene-3-carboxylate [Chem. Ber. 98, 3571 (1965)]was used in place of methyl 3-aminothiophene-2-carboxylate to obtain 8.69 g (40.7%) of Compound (g-1).

NMR(CDCl₃)δ(ppm): 7.25–7.58(1H, br), 7.02 (1H, d, J=5.4 Hz), 6.14 (1H, d, J=5.4 Hz), 3.82 (3H, s), 3.26 (2H, t, J=6.9 Hz), 1.68–1.88 (2H, m), 1.33–1.50 (2H, m), 0.96 (3H, t, J=6.9 Hz).

2) 7-n-butyl-6H-thieno [2,3-d]oxadine-4,6 (7H)-dione [Compound (g-2)]

In the same manner as in Reference Example 1-2), 8.69 g (40.7 mmol) of Compound (g-1) was used in place of Compound (a-1) to obtain 4.63 g (50.4%) of Compound (g-2).

NMR(DMSO-d₆)δ(ppm): 7.29 (2H, s), 3.85(2H, t, J=7.4 Hz), 1.65–1.76 (2H, m), 1.31–1.45 (2H, m), 0.92 (3H, t, J=7.4 Hz)

3) 7-n-butyl-4-hydroxy-5-nitrothieno [2,3-b]pyridine-6 (7H)-one [Compound (g-3)]

In the same manner as in Reference Example 1-3), 4.63 g (20.6 mmol) of Compound (g-2) was used in place of Compound (a-2) to obtain 1.78 g (32.3%) of Compound (g-3).

NMR(DMSO-d₆)δ(ppm): 7.53 (1H, d, J=5.9Hz), 7.36 (1H, d, J=5.9 Hz), 4.03 (2H, t, J=7.4 Hz), 1.64–1.75 (2H, m), 1.30–1.43 (2H, m), 0.93 (3H, t, J=7.4 Hz).

4) 4-amino -7-n-butyl -5-nitrothieno [2,3-b]pyridine-6(7H ) one [Compound (g)]

In the same manner as in Reference Examples 1–4) and 1–5), 2.06 g (7.68 mmol) of Compound (9-3) was used in place of Compound (a-3) to obtain 1.12 g (54.5%) of Compound (g).

NMR(DMSO-d₆)δ(ppm): 8.50 (2H, s), 7.74 (1H, d, J=5.9 Hz), 7.31 (1H, d, J=5.9 Hz), 3.94 (2H, t, J=7.4 Hz), 1.54–1.70 (2H, m), 1.24–1.41 (2H, m), 0.92 (3H, t, J=7.4 Hz).

REFERENCE EXAMPLE 8

4-amino-5-nitro-7-n-propylthieno[2,3-b]pyridine-6(7H)-one [Compound (h)]

1) Methyl 2-mono-n-propylaminothiophene-3-carboxylate [Compound (h-1)]

In the same manner as in Reference Example 1-1), methyl 2-aminothiophene-3-carboxylate [Chem. Bet. 98, 3571 (1965)]and n-propyl iodide were used in place of methyl 3-aminothiophene-2-carboxylate and n-butyl iodide to obtain 10.76 g (54.0%) of Compound (h-1).

2) 7-n-propyl-6H-thieno [2,3-d]oxadine-4,6 (7H )-dione [Compound (h-2)]

In the same manner as in Reference Example 1-2), 10.76 g (54.0 mmol) of Compound (h-1) was used in place of Compound (a-1) to obtain 7.16 g (62.8%) of Compound (h-2).

NMR(DMSO-d₆)δ(ppm): 7.31 (1H, d, J=5.9 Hz), 6.93 (1H, d, J=5.9 Hz), 3.93 (2H, t, J=7.4 Hz), 1.81–1.95 (2H, m), 1.04 (3H, t, J=7.4 Hz)

3) 4-hydroxy-5-nitro-7-n-propylthieno [2,3-b]pyridine-6 (7H)-one [Compound (h-3)]

In the same manner as in Reference Example 1-3), 7.16 g (33.9 mmol) of Compound (h-2) was used in place of Compound (a-2) to obtain 6.27 g (72.8%) of Compound (h-3).

4) 4-amino-5-nitro-7-n-propylthieno[2,3-b]pyridine-6(7H)-one [Compound (h)]

In the same manner as in Reference Examples 1–4) and 1–5), 5.08 g (20.0 mmol) of Compound (h-3) was used in place of Compound (a-3) to obtain 3.26 (64.4% ) of Compound (h).

NMR(DMSO-d₆)δ(ppm): 8.37 (2H, s), 7.74 (1H, d, J=5.9 Hz), 7.31 (1H, d, J=5.9 Hz), 3.91 (2H, t, J=7.4 Hz), 1.63–1.77 (2H, m), 0.92 (3H, t, J=7.4 Hz).

EFFECT OF THE INVENTION

According to the present invention, provided is a novel thienoimidazopyridone derivative having excellent bronchodilatory activity and immunoregulatory activity.

We claim:

1. A thienoimidazopyridone derivative represented by formula (I):

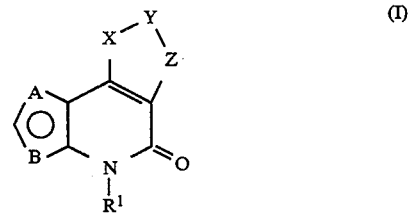

wherein A and B independently represent —S— or —CH=, X-Y-Z represents —N(R²) —CH=N— or —N=CH—N (R²)— wherein R² is hydrogen, lower alkyl or —CH(R³)—(CH₂)ₙ—R⁴ wherein R⁴ is phenyl, n is 0 or 1, and R³ is hydrogen or lower alkyl, and R¹ represents lower alkyl, or a pharmaceutically acceptable salt thereof.

2. A thienoimidazopyridone derivative according to claim 1, wherein A is —S— and B is —CH=, or a pharmaceutically acceptable salt thereof.

3. A thienoimidazopyridone derivative according to claim 1, wherein A is —CH= and B is —S—, or a pharmaceutically acceptable salt thereof.

4. A pharmaceutical composition comprising a pharmaceutically acceptable carrier and an effective amount of a thienoimidazopyridone derivative according to claim 1 or a pharmaceutically acceptable salt thereof.

* * * * *

UNITED STATES PATENT AND TRADEMARK OFFICE
CERTIFICATE OF CORRECTION

PATENT NO. : 5,342,843
DATED : August 30, 1994
INVENTOR(S) : FUMIO SUZUKI, ET AL.

It is certified that error appears in the above-identified patent and that said Letters Patent is hereby corrected as shown below:

Title page, and column 1, line 1:

IN [54] TITLE

"THIENOIMIDAZOPPYRIDONE" should read --THIENOIMIDAZOPYRIDONE--.

COLUMN 1

Line 2, "THIENOIMIDAZOPPYRIDONE" should read --THIENOIMIDAZOPYRIDONE--.

COLUMN 5

Line 10, "a" should be deleted.

COLUMN 6

Line 61, "transducers" should read --transducer--.

COLUMN 10

Line 26, "(SH)-one" should read --(5H)-one--.

COLUMN 12

Line 40, "IR(KBrcm$^{-1}$:" should read --IR(KBr)cm$^{-1}$:--.

COLUMN 13

Line 25, "4(5H)one" should read --4(5H)-one--.
Line 47, "IR(KBr cm$^{-1}$:" should read --IR(KBr)cm$^{-1}$:--.

UNITED STATES PATENT AND TRADEMARK OFFICE
CERTIFICATE OF CORRECTION

PATENT NO. : 5,342,843
DATED : August 30, 1994
INVENTOR(S) : FUMIO SUZUKI, ET AL.

It is certified that error appears in the above-identified patent and that said Letters Patent is hereby corrected as shown below:

COLUMN 15

Line 47, "[4,5-d]pyridine-(5H)-one" should read --[4,5-d]pyridine-4(5H)-one--.

COLUMN 16

Line 10, "(SH)-one" should read --(5H)-one--.
Line 21, "J=5.3HZ)," should read --J=5.3Hz),--.
Line 22, "5.74(2H,S)." should read --5.74(2H,s),--.

COLUMN 20

Line 6, "5(4H)one" should read --5(4H)-one--.
Line 14, "(0.300 tool)" should read --(0.300 mol)--.
Line 47, "4-n-butyl-7-" should read --3) 4-n-butyl-7- --.
Line 54, "in" should read --1N--.

COLUMN 22

Line 27, "4-n-propyl-" should read --2) 4-n-propyl- --.

COLUMN 23

Line 61, "5(4H)one" should read --5(4H)-one--.

COLUMN 24

Line 13, "5(4H)" should read --5(4H)- --.

UNITED STATES PATENT AND TRADEMARK OFFICE
CERTIFICATE OF CORRECTION

PATENT NO. : 5,342,843
DATED : August 30, 1994
INVENTOR(S) : FUMIO SUZUKI, ET AL.

It is certified that error appears in the above-identified patent and that said Letters Patent is hereby corrected as shown below:

COLUMN 25

Line 30, "Compound (9-3)" should read --Compound (g-3)--.
Line 46, "Bet." should read --Ber.--.

COLUMN 26

Line 16, "3.26" should read --3.26g--.

Signed and Sealed this

Ninth Day of May, 1995

BRUCE LEHMAN

Attest:

Attesting Officer

Commissioner of Patents and Trademarks